United States Patent
Li et al.

(10) Patent No.: US 7,097,985 B2
(45) Date of Patent: Aug. 29, 2006

(54) ANTIBODIES TO HUMAN CHEMOKINE BETA-9

(75) Inventors: Haodong Li, Gaithersburg, MD (US); Mark D. Adams, Rockville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 475 days.

(21) Appl. No.: 10/329,472

(22) Filed: Dec. 27, 2002

(65) Prior Publication Data

US 2005/0244888 A1    Nov. 3, 2005

Related U.S. Application Data

(60) Division of application No. 08/793,381, filed as application No. PCT/US95/06260 on Jun. 6, 1995, now Pat. No. 6,518,046, which is a continuation-in-part of application No. 08/294,251, filed on Aug. 23, 1994, now abandoned.

(51) Int. Cl.
- *G01N 33/53* (2006.01)
- *C07K 16/24* (2006.01)
- *C12N 5/12* (2006.01)

(52) U.S. Cl. .................. 435/7.1; 435/325; 435/326; 424/1.49; 530/387.1; 530/387.9; 530/387.3; 530/388.1; 530/388.15

(58) Field of Classification Search ............ 530/387.9, 530/387.1, 387.3, 388.1, 388.15; 424/1.49; 435/325, 326, 7.1

See application file for complete search history.

(56) References Cited

FOREIGN PATENT DOCUMENTS

| WO | WO-92/05198 | 4/1992 |
|---|---|---|
| WO | WO-96/25497 | 8/1996 |

OTHER PUBLICATIONS

Banas, et al., "Roles of SLC/CCL21 and CCR7 in human kidney for mesangial proliferation, migration, apoptosis, and tissue homeostasis," *J. Immunol.*, 168(9):4301-4307 (May 1, 2002).
Bischoff, et al., "Monocyte chemotactic protein 1 is a potent activator of human basophils," *J. Exp. Med.*, 175:1271-1275 (May 1992).
Blum, et al., "Three human homologs of a murine gene encoding an inhibitor of stem cell proliferation," *DNA & Cell Bio.*, 9(8):589-602 (1990).
Bonacchi, et al., "The chemokine CCL21 modulates lymphocyte recruitment and fibrosis in chronic hepatitis C," *Gastroenterology*, 125(4):1060-1076 (Oct. 2003).
Christopherson, et al., "Endothelial induction of the T-cell chemokine CCL21 in T-cell autoimmune diseases," *Blood*, 101(3):801-806 (Feb. 1, 2003).
Cook, et al., "Requirement of MIP-1 α for an inflammatory response to viral infection," *Science*, 269:1583-1585 (Sep. 15, 1995).
Clements, et al., "Biological and structural properties of MIP-1 α expressed in yeast," *Cytokine*, 4(1):76-82 (Jan. 1992).
Dausset, et al., "The CEPH YAC library," *Behring Inst. Mitt.*, 91:13-20 (Apr. 1992).
Graham, et al., "SCI/MIP-1 α:a potent stem cell inhibitor with potential roles in development," *Devel. Bio.*, 151:377-381 (Jun. 1992).
Higgins, et al., "CLUSTAL: a package for performing multiple sequence alignment on a microcomputer," *Gene*, 73:237-244 (1988).
Hisada, et al., "Synergistic antitumor effect by coexpression of chemokine CCL21/SLC and costimulatory molecule LIGHT," *Cancer Gene Ther.*, 11(4):280-288 (Apr. 2004).
Horuk, R., "Molecular properties of the chemokine receptor family," *Trends Pharmacol. Sci.*, 15(5):159-165 (May 1994).
Hromas, et al., "The chemokine CCL21 protects normal marrow progenitors from Ara-C cytotoxicity," *Cancer Chemother. Pharmacol.*, 50(2):163-166 (Aug. 2002).
Jose, et al., "Eotaxin: a potent eosinophil chemoattractant cytokine detected in a guinea pig model of allergic airways inflammation," *Journal of Experimental Medicine*, 179:881-887 (Mar. 1994).
Jose, et al., "Eotaxin: cloning of an eosinophil chemoattractant cytokine and increased mRNA expression in allergen-challenged guinea-pig lungs," *Biochemical and Biophisical Research Communications*, 205:788-794 (Nov. 30, 1994).
Kuna, et al., "Monocyte chemotactic and activating factor is a potent histamine-releasing factor for human basopils," *J. Exp. Med.*, 175:489-493 (Feb. 1992).
Kwon, et al., "cDNA sequences of two inducible T-cell genes," *Proc. Natl. Acad. Sci. USA*, 86:1963-1967 (Mar. 1989).
Matsushima, et al., "Purification and characterization of a novel monocyte chemotactic and activating factor produced by a human myelomonocytic cell line," *J. Exp. Med.*, 169:1485-1490 (Apr. 1989).
Mikayama, et al., "Molecular cloning and functional expression of a cDNA encoding glycosylation-inhibiting factor," *Proc. Natl. Acad. Sci. USA*, 90(21):10056-10060 (Nov. 1, 1993).

(Continued)

*Primary Examiner*—Prema Mertz
(74) *Attorney, Agent, or Firm*—Human Genome Sciences, Inc.

(57) ABSTRACT

Human Ckβ-9 polypeptides and DNA (RNA) encoding such chemokine polypeptides and a procedure for producing such polypeptides by recombinant techniques is disclosed. Also disclosed are methods for utilizing such Ckβ-9 polypeptides for the treatment of leukemia, tumors, chronic infections, autoimmune disease, fibrotic disorders, wound healing and psoriasis. Antagonists against such polypeptides and their use as a therapeutic to treat rheumatoid arthritis, autoimmune and chronic inflammatory and infective diseases, allergic reactions, prostaglandin-independent fever and bone marrow failure are also disclosed. Diagnostic assays are also disclosed which detect the presence of mutations in the Ckβ-9 coding sequence and over-expression of the Ckβ-9 protein.

23 Claims, 2 Drawing Sheets

OTHER PUBLICATIONS

Nagira, et al., "Molecular cloning of a novel human CC chemokine secondary lymphoid-tissue chemokine that is a potent chemoattractant for lymphocytes and mapped to chromosome 9p13," *J. Biol. Chem.*, 272(31):19518-19524 (Aug. 1, 1997).

Naruse, et al., "A YAC contig of the human CC chemokine genes clustered on chromosome 17q11.2," *Genomics*, 34(2):236-240 (Jun. 1, 1996).

Nomura, et al., "Chemokines and anti-cancer immunotherapy: anti-tumor effect of EBI1-ligand chemokine (ELC) and secondary lymphoid tissue chemokine (SLC)," *Anticancer Research*, 20:4073-4808 (2000).

Obaru, et al., "A cDNA clone used to study mRNA inducible in human tonsillar lymphocytes by a tumor promoter," *J. Biochem.*, 99(3):885-894 (1986).

Parkinson, et al., "Hemopoietic stem cell inhibitor (SCI/MIP-1 alpha) also inhibits clonogenic epidermal keratinocyte proliferation," *J. Invest. Dermatol.*, 101(2):113-117 (Aug. 1993).

Research Genetics (advt.), *Genomics*, 16(3), Cover iv (Jun. 1993).

Research Genetics, Online Catalog, www/resgen.com, "Human YAC Resources," Accessed Sep. 8, 1998.

Rothenburg, et al., "Constitutive and allergen-induced expression of eotaxin mRNA in the guinea pig lung," *Journal of Experimental Medicine*, 181:1211-1216 (Mar. 1995).

Schall, "Biology of the RANTES/SIS cytokine family," *Cytokine*, 3(3):165-183 (May 1991).

Taub, et al., "Preferential migration of activated CD4+ and CD8+ T cells in response to MIP-1 alpha and MIP-1 beta," *Science*, 260(5106):355-358 (Apr. 16, 1993).

Vicari, et al., "Antitumor effects of the mouse chemokine 6Ckine/SLC through angiostatic and immunological mechanisms," *J. Immunol.*, 165:1992-2000 (2000).

Villiger, et al., "Monocyte chemoattractant protein-1 (MCP-1) expression in human articular cartilage. Induction by peptide regulatory factors and differential effects of dexamethasone and retinoic acid," *J. Clin. Invest.*, 90(2):488-496 (Aug. 1992).

Voet, et al., *Biochemistry*, John Wiley & Sons, pp. 126-128 and 228-234.

Wempe, et al., "Gene expression and cDNA cloning identified a major basic protein constituent of bovine seminal plasma as bovine monocyte-chemoattractant protein-1 (MCP-1)" *DNA Cell Biol.*, 10(9):671-679 (Nov. 1991).

Weninger, et al., "Naive T cell recruitment to nonlymphoid tissues; a role for endothelium-expressed CC chemokine ligand 21 in autoimmune disease and lymphoid neogenesis," *J. Immunol.*, 170(9):4638-4648 (May 1, 2003).

Wolpe, et al., "Macrophage inflammatory proteins 1 and 2: members of a novel superfamily of cytokines," *FASEB*, 3:2565-2573 (Dec. 1989).

Zipfel, et al., "Mitotic activation of human T-cells induces two closely related genes which share structural similarities with a new family of secreted factors," *J. Immunol.*, 142(5):1582-1590 (Mar. 1, 1989).

Zhou, et al., "Macrophage inflammatory protein-1 alpha rapidly modulates its receptors and inhibits the anti-CD3 mAb-mediated proliferation of T lymphocytes," *J. Immunol.*, 151(8):4333-4341 (Oct. 15, 1993).

Figure 1

```
ATGGCTCAGTCACTGGCTCTGAGCCTCCTTATCCTGGTTCTGGCCTTTGGCATCCCCAGG
 M  A  Q  S  L  A  L  S  L  L  I  L  V  L  A  F  G  I  P  R

ACCCAAGGCAGTGATGGAGGGCTCAGGACTGTTGCCTCAAGTACAGCCAAAGGAAGATT
 T  Q  G  S  D  G  G  A  Q  D  C  C  L  K  Y  S  Q  R  K  I

CCCGCCAAGGTTGTCGTCCGCAGCTACCGGAAGCAGGAACCAAGCTTAGGCTGCTCCATCCCA
 P  A  K  V  V  R  S  Y  R  K  Q  E  P  S  L  G  C  S  I  P

GCTATCCTGTTCTTGCCCCGCAAGCGCTCTCAGGCAGAGCTATGTGCAGACCCAAAGGAG
 A  I  L  F  L  P  R  K  R  S  Q  A  E  L  C  A  D  P  K  E

CTCTGGGTGCAGCAGCTGATGCAGCATCTGGACAAGACACCATCCCCACAGAAACCAGCC
 L  W  V  Q  Q  L  M  Q  H  L  D  K  T  P  S  P  Q  K  P  A

CAGGGCTGCAGGAAGGACAGGGGCCTCCAAGACTGGCAAGAAAGGAAAGGGCTCCAAA
 Q  G  C  R  K  D  R  G  A  S  K  T  G  K  K  G  K  G  S  K

GGCTGCAAGAGAGACTGAGCGGTCACAGACCCCTAAAGGGGCCATAG
 G  C  K  R  T  E  R  S  Q  T  P  K  G  P  *
```

Figure 2

```
25  DGGAQDCCLKYSQ.RKIPAKVVRSYRKQEPSLGCSIPAILFLPRKRSQAE  73
    .|:.||:.       .|:    :.|| ||  .|||   |:
 2  PGIPSACCFRVTNICKISFQALKSY.KIITSSKCPQTAIVF..EIKPDKM  48

74  LCADPKELWVQQLMQHLDKTPSPQKP  99
    :|||||   ||:   :..:|  |:|
49  ICADPRXXWVQDAKKYLDQISQXTKP  74
```

ANTIBODIES TO HUMAN CHEMOKINE BETA-9

CROSS REFERENCE TO RELATED APPLICATIONS

This application is a divisional of U.S. patent application No. 08/793,381, filed May 19, 1997 (now U.S. Pat. No. 6,518,046), which is the U.S. national stage of International Application No. PCT/US95/06260, filed Jun. 6, 1995, which is a continuation-in-part of and claims priority under 35 U.S.C. § 120 to U.S. application No. 08/294,251, filed Aug. 23, 1994 (now abandoned).

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human chemokine beta-9 sometimes hereinafter referred to as "Ckβ-9". The invention also relates to inhibiting the action of such polypeptides.

BACKGROUND OF THE INVENTION

Chemokines, also referred to as intercrine cytokines, are a subfamily of structurally and functionally related cytokines. These molecules are 8–10 kd in size. In general, chemokines exhibit 20% to 75% homology at the amino acid level and are characterized by four conserved cysteine residues that form two disulfide bonds. Based on the arrangement of the first two cysteine residues, chemokines have been classified into two subfamilies, alpha and beta. In the alpha subfamily, the first two cysteines are separated by one amino acid and hence are referred to as the "C—X—C" subfamily. In the beta subfamily, the two cysteines are in an adjacent position and are, therefore, referred to as the "C—C" subfamily. Thus far, at least eight different members of this family have been identified in humans.

The intercrine cytokines exhibit a wide variety of functions. A hallmark feature is their ability to elicit chemotactic migration of distinct cell types, including monocytes, neutrophils, T lymphocytes, basophils and fibroblasts. Many chemokines have pro-inflammatory activity and are involved in multiple steps during an inflammatory reaction. These activities include stimulation of histamine release, lysosomal enzyme and leukotriene release, increased adherence of target immune cells to endothelial cells, enhanced binding of complement proteins, induced expression of granulocyte adhesion molecules and complement receptors, and respiratory burst. In addition to their involvement in inflammation, certain chemokines have been shown to exhibit other activities. For example, macrophage inflammatory protein 1 (MIP-1) is able to suppress hematopoietic stem cell proliferation, platelet factor-4 (PF-4) is a potent inhibitor of endothelial cell growth, Interleukin-3 (IL-8) promotes proliferation of keratinocytes, and GRO is an autocrine growth factor for melanoma cells.

In light of the diverse biological activities, it is not surprising that chemokines have been implicated in a number of physiological and disease conditions, including lymphocyte trafficking, wound healing, hematopoietic regulation and immunological disorders such as allergy, asthma and arthritis.

Members of the "C—C" branch exert there effects on the following cells: eosinophils which destroy parasites to lessen parasitic infection and cause chronic inflammation in the airways of the respiratory system; macrophages which suppress tumor formation in vertebrates; and basophils which release histamine which plays a role in allergic inflammation. However, members of one branch may exert an effect on cells which are normally responsive to the other branch of chemokines and, therefore, no precise role can be attached to the members of the branches.

While members of the C—C branch act predominantly on mononuclear cells and members of the C—X—C branch act predominantly on neutrophils a distinct chemoattractant property cannot be assigned to a chemokine based on this guideline. Some chemokines from one family show characteristics of the other.

SUMMARY OF THE INVENTION

The polypeptide of the present invention has been putatively identified as Ckβ-9 based on amino acid sequence homology.

In accordance with one aspect of the present invention, there are provided novel polypeptides as well as biologically active and diagnostically or therapeutically useful fragments, analogs and derivatives thereof. The polypeptide of the present invention is of human origin.

In accordance with another aspect of the present invention, there are provided isolated nucleic acid molecules encoding the polypeptide of the present invention, including mRNAs, DNAs, cDNAs, genomic DNAs as well as analogs and biologically active and diagnostically or therapeutically useful fragments and derivatives thereof.

In accordance with yet a further aspect of the present invention, there is provided a process for producing such polypeptides by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptides, or polynucleotides encoding such polypeptides for therapeutic purposes, for example, to treat solid tumors, chronic infections, auto-immune diseases, psoriasis, asthma, allergy, to regulate hematopoiesis, and to promote wound healing.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, in the treatment of auto-immune diseases, chronic inflammatory diseases, histamine-mediated allergic reactions, asthma, arthritis, prostaglandin-independent fever, bone marrow failure, silicosis, sarcoidosis, hypereosinophilic syndrome and lung inflammation.

In accordance with yet a further aspect of the present invention, there are also provided nucleic acid probes comprising nucleic acid molecules of sufficient length to specifically hybridize to a nucleic acid sequence of the present invention.

In accordance with still another aspect of the present invention, there are provided diagnostic assays for detecting diseases related to the expression of the polypeptide and mutations in the nucleic acid sequences encoding such polypeptide.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 displays the cDNA sequence (SEQ ID NO:1) and corresponding deduced amino acid sequence (SEQ ID NO:2) of Ckβ-9. The initial 23 amino acids represent the leader sequence such that the putative mature polypeptide comprises 111 amino acids. The standard one-letter abbreviation for amino acids is used.

FIG. 2 displays the amino acid sequence homology between Ckβ-9 (SEQ ID NO:2) and the mature peptide of eotaxin (bottom) (SEQ ID NO:7).

DETAILED DESCRIPTION

In accordance with an aspect of the present invention, there are provided isolated nucleic acids (polynucleotides) which encode for the mature polypeptides having the deduced amino acid sequences of FIG. 1 (SEQ ID NO:2) or for the mature polypeptide encoded by the cDNA of the clones deposited with the American Type Culture Collection (ATCC), 10801 University Boulevard, Manassas, Va. 20110-2209 (present address) as ATCC Deposit No. 75803 on Jun. 7, 1994.

The polynucleotide encoding Ckβ-9 was discovered in a cDNA library derived from a human breast lymph node. Ckβ-9 is structurally related to the chemokine family. It contains an open reading frame encoding a protein of 134 amino acid residues of which approximately the first 23 amino acids residues are the putative leader sequence such that the mature protein comprises 111 amino acids. The protein exhibits the highest degree of homology to eotaxin with 32% identity and 69% similarity over a stretch of 75 amino acid residues. It is also important that the four spatially conserved cysteine residues in chemokines are found in the polypeptides of the present invention.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptides may be identical to the coding sequence shown in FIG. 1 (SEQ ID NO:1) or that of the deposited clones or may be a different coding sequence which coding sequence, as a result of the redundancy or degeneracy of the genetic code, encodes the same mature polypeptides as the DNA of FIG. 1 (SEQ ID NO:1) or the deposited cDNA.

The polynucleotides which encodes for the mature polypeptides of FIG. 1 (SEQ ID NO:2) or for the mature polypeptides encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptides.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clones. The variant of the polynucleotides may be a naturally occurring allelic variant of the polynucleotides or a non-naturally occurring variant of the polynucleotides.

Thus, the present invention includes polynucleotides encoding the same mature polypeptides as shown in FIG. 1 (SEQ ID NO:2) or the same mature polypeptides encoded by the cDNA of the deposited clones as well as variants of such polynucleotides which variants encode for a fragment, derivative or analog of the polypeptides of FIG. 1 (SEQ ID NO:2) or the polypeptides encoded by the cDNA of the deposited clones. Such nucleotide variants include deletion variants, substitution variants and addition or insertion variants.

As hereinabove indicated, the polynucleotides may have a coding sequence which is a naturally occurring allelic variant of the coding sequence shown in FIG. 1 (SEQ ID NO:2) or of the coding sequence of the deposited clones. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptides may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptides of the present invention. The marker sequence may be a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to chemokine polypeptides which have the deduced amino acid sequences of FIG. 1 (SEQ ID NO:2) or which has the amino acid sequence encoded by the deposited cDNA, as well as fragments, analogs and derivatives of such polypeptides.

The terms "fragment," "derivative" and "analog" when referring to the polypeptides of FIG. 1 (SEQ ID NO:2) or that encoded by the deposited cDNA, means polypeptides which retain essentially the same biological function or activity as such polypeptides. Thus, an analog includes a proprotein which can be activated by cleavage of the proprotein portion to produce an active mature polypeptide.

The chemokine polypeptides of the present invention may be recombinant polypeptides, natural polypeptides or a synthetic polypeptides, preferably recombinant polypeptides.

The fragment, derivative or analog of the polypeptides of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 90% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the Ckβ-9 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The Ckβ-9 polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The Ckβ-9 polypeptides may be employed to inhibit bone marrow stem cell colony formation as adjunct protective treatment during cancer chemotherapy and for leukemia.

The chemokine polypeptides may also be used to inhibit epidermal keratinocyte proliferation for treatment of psoriasis, which is characterized by keratinocyte hyper-proliferation.

The chemokine polypeptides may also be used to treat solid tumors by stimulating the invasion and activation of host defense cells, e.g., cytotoxic T cells and macrophages. They may also be used to enhance host defenses against resistant chronic infections, for example, mycobacterial infections via the attraction and activation of microbicidal leukocytes.

The chemokine polypeptides may also be used to treat auto-immune disease and lymphocytic leukemia by inhibiting T cell proliferation by the inhibition of IL2 biosynthesis.

Ckβ-9 may also be used in wound healing, both via the recruitment of debris clearing and connective tissue promoting inflammatory cells and also via its control of excessive TGF-mediated fibrosis. In this same manner, Ckβ-9 may also be used to treat other fibrotic disorders, including liver cirrhosis, osteoarthritis and pulmonary fibrosis.

The chemokine polypeptides also increase the presence of eosinophils which have the distinctive function of killing the larvae of parasites that invade tissues, as in schistosomiasis, trichinosis and ascariasis.

They may also be used to regulate hematopoiesis, by regulating the activation and differentiation of various hematopoietic progenitor cells, for example, to release mature leukocytes from the bone marrow following chemotherapy.

The polynucleotides and polypeptides encoded by such polynucleotides may also be utilized for in vitro purposes related to scientific research, synthesis of DNA and manufacture of DNA vectors and for designing therapeutics and diagnostics for the treatment of human disease.

Fragments of the full length Ckβ-9 genes may be used as a hybridization probe for a cDNA library to isolate the full length gene and to isolate other genes which have a high sequence similarity to the gene or similar biological activity. Probes of this type can be, for example, between 20 and 2000 bases. Preferably, however, the probes have between 30 and 50 base pairs. The probe may also be used to identify a cDNA clone corresponding to a full length transcript and a genomic clone or clones that contain the complete genes including regulatory and promoter regions, exons, and introns. An example of a screen comprises isolating the coding region of the genes by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

This invention is also related to the use of the Ckβ-9 gene as part of a diagnostic assay for detecting diseases or susceptibility to diseases related to the presence of mutations in the Ckβ-9 nucleic acid sequences. Such diseases are related to under-expression of the chemokine polypeptides, for example, tumors and cancers.

Individuals carrying mutations in the Ckβ-9 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding Ckβ-9 can be used to identify and analyze Ckβ-9 mutations. For example, deletions and insertions can be detected by a change in size of the amplified product in comparison to the normal genotype. Point mutations can be identified by hybridizing amplified DNA to radiolabeled Ckβ-9 RNA or alternatively, radiolabeled Ckβ-9 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of Ckβ-9 protein in various tissues since an over-expression of the proteins compared to normal control tissue samples may detect the presence of a disease or susceptibility to a disease, for example, a tumor. Assays used to detect levels of Ckβ-9 protein in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the Ckβ-9 antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like bovine serum albumin. Next, the monoclonal antibody is incubated in the dish during which time the monoclonal antibodies attach to any Ckβ-9 proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to Ckβ-9. Unattached reporter antibody is then washed out. Peroxidase substrates are then added to the dish and the amount of color developed in a given time period is a measurement of the amount of Ckβ-9 protein present in a given volume of patient sample when compared against a standard curve.

A competition assay may be employed wherein antibodies specific to Ckβ-9 are attached to a solid support and labeled Ckβ-9 and a sample derived from the host are passed over the solid support and the amount of label detected, for example by liquid scintillation chromatography, can be correlated to a quantity of Ckβ-9 in the sample.

A "sandwich" assay is similar to an ELISA assay. In a "sandwich" assay Ckβ-9 is passed over a solid support and binds to antibody attached to a solid support. A second antibody is then bound to the Ckβ-9. A third antibody which is labeled and specific to the second antibody is then passed over the solid support and binds to the second antibody and an amount can then be quantified.

This invention provides a method for identification of the receptors for Ckβ-9 polypeptides. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photo-affinity linked with cell membrane or extract preparations that express the receptor molecule. Cross-linked material is resolved by PAGE analysis and exposed to x-ray film. The labeled complex containing the receptors of the polypeptides can be excised, resolved into peptide fragments, and subjected to protein micro-sequencing. The amino acid sequence obtained from micro-sequencing would be used to design a set of degenerate oligonucleotide probes to screen a cDNA library to identify the genes encoding the putative receptors.

This invention provides a method of screening compounds to identify agonists and antagonists to the Ckβ-9 polypeptides of the present invention. An agonist is a compound which has similar biological functions of the polypeptides, while antagonists block such functions. Chemotaxis may be assayed by placing cells, which are chemo-attracted by either of the polypeptides of the present invention, on top of a filter with pores of sufficient diameter to admit the cells (about 5 m). Solutions of potential agonists are placed in the bottom of the chamber with an appropriate control medium in the upper compartment, and thus a concentration gradient of the agonist is measured by counting cells that migrate into or through the porous membrane over time.

When assaying for antagonists, the polypeptides of the present invention are placed in the bottom chamber and the potential antagonist is added to determine if chemotaxis of the cells is prevented.

Alternatively, a mammalian cell or membrane preparation expressing the receptors of the polypeptides would be incubated with a labeled Ckβ-9 polypeptide, e.g. radioactivity, in the presence of the compound. The ability of the compound to block this interaction could then be measured. When assaying for agonists in this fashion, the chemokines would be absent and the ability of the agonist itself to interact with the receptor could be measured.

Examples of potential Ckβ-9 antagonists include antibodies, or in some cases, oligonucleotides, which bind to the polypeptides. Another example of a potential antagonist is a negative dominant mutant of the polypeptides. Negative dominant mutants are polypeptides which bind to the receptor of the wild-type polypeptide, but fail to retain biological activity.

Antisense constructs prepared using antisense technology are also potential antagonists. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple-helix, see Lee et al., Nucl. Acids Res., 6:3073 (1979); Cooney et al, Science, 241:456 (1988); and Dervan et al., Science, 251: 1360 (1991)), thereby preventing transcription and the production of the chemokine polypeptides. The antisense RNA oligonucleotide hybridizes to the mRNA in vivo and blocks translation of the mRNA molecule into the polypeptides (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of Ckβ-9.

Another potential Ckβ-9 antagonist is a peptide derivative of the polypeptides which are naturally or synthetically modified analogs of the polypeptides that have lost biological function yet still recognize and bind to the receptors of the polypeptides to thereby effectively block the receptors. Examples of peptide derivatives include, but are not limited to, small peptides or peptide-like molecules.

The antagonists may be employed to inhibit the chemotaxis and activation of macrophages and their precursors, and of neutrophils, basophils, B lymphocytes and some T cell subsets, e.g., activated and CD8 cytotoxic T cells and natural killer cells, in auto-immune and chronic inflammatory and infective diseases. Examples of auto-immune diseases include rheumatoid arthritis, multiple sclerosis, and insulin-dependent diabetes. Some infectious diseases include silicosis, sarcoidosis, idiopathic pulmonary fibrosis by preventing the recruitment and activation of mononuclear phagocytes, idiopathic hypereosinophilic syndrome by preventing eosinophil production and migration, endotoxic shock by preventing the migration of macrophages and their production of the chemokine polypeptides of the present invention.

The antagonists may also be employed for treating atherosclerosis, by preventing monocyte infiltration in the artery wall.

The antagonists may also be employed to treat histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated.

The antagonists may also be employed to treat chronic and acute inflammation by preventing the attraction of monocytes to a wound area. They may also be employed to regulate normal pulmonary macrophage populations, since acute and chronic inflammatory pulmonary diseases are associated with sequestration of mononuclear phagocytes in the lung.

Antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies.

The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by chemokines.

The antagonists may also be employed to treat cases of bone marrow failure, for example, aplastic anemia and myelodysplastic syndrome.

The antagonists may also be used to treat asthma and allergy by preventing eosinophil accumulation in the lung. The antagonists may also be employed to treat subepithelial basement membrane fibrosis which is a prominent feature of the asthmatic lung.

The antagonists may be employed in a composition with a pharmaceutically acceptable carrier, e.g., as hereinafter described.

The Ckβ-9 polypeptides and agonists and antagonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides and agonists and antagonists may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The pharmaceutical compositions are administered in an amount which is effective for treating and/or prophylaxis of the specific indication. In general, the polypeptides will be administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The Ckβ-9 polypeptides, and agonists or antagonists which are polypeptides, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37 C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of Ckβ-9

The DNA sequence encoding for Ckβ-9, ATCC #75803, is initially amplified using PCR oligonucleotide primers corresponding to the 5' and 3' end sequences of the processed Ckβ-9 gene (minus the putative signal peptide sequence). Additional nucleotides corresponding to Ckβ-9 were added to the 5' and 3' end sequences, respectively. The 5' oligonucleotide primer has the sequence 5' CCCGCATGC GTGATGGAGGGGCTCAG 3' (SEQ ID NO:3) contains a SphI restriction enzyme site (bold) followed by 17 nucleotides of Ckβ-9 coding sequence (underlined) starting from the second nucleotide of the sequences coding for the mature protein. The ATG codon is included in the SphI site. In the next codon following the ATG, the first base is from the SphI site and the remaining two bases correspond to the second and third base of the first codon (residue $S_{24}$) of the putative mature protein. As a consequence, the first base in this codon is changed from A to C comparing with the original sequences, resulting in an S to R substitution in the recombinant protein. The 3' sequence 5' AAAGGATCCTGGC-CCTTTAGGGGTCTGTGA 3' (SEQ ID NO:4) contains complementary sequences to a BamH1 site (bold) and is followed by 21 nucleotides of gene specific sequences preceding the termination codon. The restriction enzyme sites correspond to the restriction enzyme sites on the bacterial expression vector pQE-70 (Qiagen, Inc. Chatsworth, Calif.). pQE-70 encodes antibiotic resistance ($Amp^r$), a bacterial origin of replication (ori), an IPTG-regulatable promoter operator (P/O), a ribosome binding site (RBS), a 6-His tag and restriction enzyme sites. pQE-70 is then digested with SphI and BamH1. The amplified sequences are ligated into pQE-9 and inserted in frame with the sequence encoding for the histidine tag and the RBS. The ligation mixture is then used to transform the *E. coli* strain M15/rep4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl pH 5.0. After clarification, solubilized Ckβ-9 is purified from this solution by chromatography on a Nickel-Chelate column under conditions that allow for tight binding by proteins containing the 6-His tag (Hochuli, E. et al., J. Chromatography 411:177–184 (1984)). Ckβ-9 (>98% pure) is eluted from the column in 6M guanidine HCl. Protein renaturation out of GnHCl can be accomplished by several protocols (Jacnicke, R. and Rudolph, R., Protein Structure—A Practical Approach, IRL Press, New York (1990)). Initially, step dialysis is utilized to remove the GnHCL. Alternatively, the purified protein isolated from the Ni-chelate column can be bound to a second column over which a decreasing linear GnHCL gradient is run. The protein is allowed to renature while bound to the column and is subsequently eluted with a buffer containing 250 mM Imidazole, 150 mM NaCl, 25 mM Tris-HCl pH 7.5 and 10% Glycerol. Finally, soluble protein is dialyzed against a storage buffer containing 5 mM Ammonium Bicarbonate.

EXAMPLE 2

Expression of Recombinant Ckβ-9 in COS cells

The expression of plasmid, Ckβ-9 HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire Ckβ-9 precursor and a HA tag fused in frame to its 3' end is cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding for Ckβ-9, ATTC #75803, is constructed by PCR using two primers: the 5' primer 5' AAAGGATCCAGACATGGCTCAGTCACT 3' (SEQ ID NO:5) contains a BamH1 site followed by 18 nucleotides of Ckβ-9 coding sequence starting from the initiation codon; the 3' sequence 5' CGCTCTAGATCAAGCGTAGTCTGG-GACGTCGTATGGGTATGGCCCTTTAGGGG TCTG 3' (SEQ ID NO:6) contains complementary sequences to XbaI site, translation stop codon, HA tag and the last 18 nucleotides of the Ckβ-9 coding sequence (not including the stop codon). Therefore, the PCR product contains a BamH1 site, Ckβ-9 coding sequence followed by HA tag fused in frame, a translation termination stop codon next to the HA tag, and an XbaI site. The PCR amplified DNA fragment and the vector, pcDNAI/Amp, are digested with BamH1 and XbaI restriction enzyme and ligated. The ligation mixture is transformed into E. coli strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant Ckβ-9, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the Ckβ-9 HA protein is detected by radiolabelling and immunoprecipitation method (E. Harlow, D. Lane, Antibodies: A Laboratory Manual, Cold Spring Harbor Laboratory Press, (1988)). Cells are labeled for 8 hours with $^{35}$S-cysteine two days post transfection. Culture media is then collected and cells are lysed with detergent (RIPA buffer (150 mM NaCl, 1% NP-40, 0.1% SDS, 1% NP-40, 0.5% DOC, 50mM Tris, pH 7.5) (Wilson, I. et al., Id. 37:767 (1984)). Both cell lysate and culture media are precipitated with a HA specific monoclonal antibody. Proteins precipitated are analyzed by SDS-PAGE.

EXAMPLE 3

Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated antibody or fragment thereof that specifically binds to a protein selected from the group consisting of:
   (a) a protein whose amino acid sequence consists of amino acid residues 1 to 134 of SEQ ID NO:2;
   (b) a protein whose amino acid sequence consists of amino acid residues 24 to 134 of SEQ ID NO:2;
   (c) a protein whose amino acid sequence consists of a portion of SEQ ID NO:2, wherein said portion is at least 30 contiguous amino acid residues in length; and
   (d) a protein whose amino acid sequence consists of a portion of SEQ ID NO:2, wherein said portion is at least 50 contiguous amino acid residues in length.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 1 that specifically binds protein (d).

6. The antibody or fragment thereof of claim 2 that specifically binds protein (c).

7. The antibody or fragment thereof of claim 3 wherein said protein bound by said antibody or fragment thereof is glycosylated.

8. The antibody or fragment thereof of claim 3 wherein said antibody or fragment thereof is human 9. The antibody or fragment thereof of claim 3 wherein said antibody or fragment thereof is polyclonal.

10. The antibody or fragment thereof of claim 3 wherein said antibody or fragment thereof is monoclonal.

11. The antibody or fragment thereof of claim 3 which is selected from the group consisting of:
    (a) a chimeric antibody or fragment thereof;
    (b) a humanized antibody or fragment thereof;
    (c) a single chain antibody; and
    (d) a Fab fragment.

12. The antibody or fragment thereof of claim 3 which is radiolabeled.

13. The antibody or fragment thereof of claim 3 wherein said antibody or fragment thereof specifically binds to said protein in a Western blot or an ELISA.

14. An isolated cell that produces the antibody or fragment thereof of claim 3.

15. A hybridoma that produces the antibody or fragment thereof of claim 3.

16. A method of detecting Ckβ-9 protein in a biological sample comprising:
    (a) contacting the biological sample with the antibody or fragment thereof of claim 3; and
    (b) detecting the Ckβ-9 protein in the biological sample.

17. An isolated antibody or fragment thereof that specifically binds a Ckβ-9 protein wherein said Ckβ-9 protein is purified from a cell culture and is encoded by a polynucleotide encoding amino acids 1 to 134 of SEQ ID NO:2.

18. The antibody or fragment thereof of claim 17 wherein said antibody or fragment thereof is monoclonal.

19. The antibody or fragment thereof of claim 17 wherein said antibody or fragment thereof is polyclonal.

20. The antibody or fragment thereof of claim 17 wherein said antibody or fragment thereof is human.

21. The antibody or fragment thereof of claim 17 which is selected from the group consisting of:
    (a) a chimeric antibody or fragment thereof;
    (b) a humanized antibody or fragment thereof;
    (c) a single chain antibody; and
    (d) a Fab fragment.

22. The antibody or fragment thereof of claim 17 wherein said antibody or fragment thereof specifically binds to said protein in a Western blot or an ELISA.

23. The antibody or fragment thereof of claim 17 wherein the amino acid sequence of said Ckβ-9 protein consists of amino acid residues 24 to 134 of SEQ ID NO:2.

* * * * *

SEQUENCE LISTING

<160> NUMBER OF SEQ ID NOS: 7

<210> SEQ ID NO 1
<211> LENGTH: 405
<212> TYPE: DNA
<213> ORGANISM: Homo sapiens

<400> SEQUENCE: 1

```
atggctcagt cactggctct gagcctcctt atcctggttc tggcctttgg catccccagg      60
acccaaggca gtgatggagg ggctcaggac tgttgcctca agtacagcca aggaagatt     120
cccgccaagg ttgtccgcag ctaccggaag caggaaccaa gcttaggctg ctccatccca    180
gctatcctgt tcttgccccg caagcgctct caggcagagc tatgtgcaga cccaaaggag    240
ctctgggtgc agcagctgat gcagcatctg acaagacac catccccaca gaaaccagcc     300
cagggctgca ggaaggacag gggggcctcc aagactggca agaaggaaa gggctccaaa     360
ggctgcaaga ggactgagcg gtcacagacc cctaaagggc catag                    405
```

<210> SEQ ID NO 2
<211> LENGTH: 134
<212> TYPE: PRT
<213> ORGANISM: Homo sapiens

<400> SEQUENCE: 2

```
Met Ala Gln Ser Leu Ala Leu Ser Leu Leu Ile Leu Val Leu Ala Phe
 1               5                  10                  15

Gly Ile Pro Arg Thr Gln Gly Ser Asp Gly Ala Gln Asp Cys Cys
             20                  25                  30

Leu Lys Tyr Ser Gln Arg Lys Ile Pro Ala Lys Val Val Arg Ser Tyr
         35                  40                  45

Arg Lys Gln Glu Pro Ser Leu Gly Cys Ser Ile Pro Ala Ile Leu Phe
     50                  55                  60

Leu Pro Arg Lys Arg Ser Gln Ala Glu Leu Cys Ala Asp Pro Lys Glu
 65                  70                  75                  80

Leu Trp Val Gln Gln Leu Met Gln His Leu Asp Lys Thr Pro Ser Pro
                 85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130
```

<210> SEQ ID NO 3
<211> LENGTH: 26
<212> TYPE: DNA
<213> ORGANISM: Artificial sequence
<220> FEATURE:
<223> OTHER INFORMATION: Contains a SphI restriction site

<400> SEQUENCE: 3

```
cccgcatgcg tgatggaggg gctcag                                          26
```

<210> SEQ ID NO 4
<211> LENGTH: 30

```
<212> TYPE: DNA
<213> ORGANISM: Artificial sequence
<220> FEATURE:
<223> OTHER INFORMATION: Contains a BamHI site

<400> SEQUENCE: 4
aaaggatcct ggccctttag gggtctgtga                                              30

<210> SEQ ID NO 5
<211> LENGTH: 27
<212> TYPE: DNA
<213> ORGANISM: Artificial sequence
<220> FEATURE:
<223> OTHER INFORMATION: Contains a BamHI site

<400> SEQUENCE: 5
aaaggatcca gacatggctc agtcact                                                 27

<210> SEQ ID NO 6
<211> LENGTH: 57
<212> TYPE: DNA
<213> ORGANISM: Artificial sequence
<220> FEATURE:
<223> OTHER INFORMATION: Contains an XbaI site, stop codon, and HA tag

<400> SEQUENCE: 6
cgctctagat caagcgtagt ctgggacgtc gtatgggtat ggccctttag gggtctg               57

<210> SEQ ID NO 7
<211> LENGTH: 73
<212> TYPE: PRT
<213> ORGANISM: Homo sapiens
<220> FEATURE:
<221> NAME/KEY: MISC_FEATURE
<222> LOCATION: (54)..(54)
<223> OTHER INFORMATION: Xaa equals any amino acid
<220> FEATURE:
<221> NAME/KEY: MISC_FEATURE
<222> LOCATION: (55)..(55)
<223> OTHER INFORMATION: Xaa equals any amino acid
<220> FEATURE:
<221> NAME/KEY: MISC_FEATURE
<222> LOCATION: (70)..(70)
<223> OTHER INFORMATION: Xaa equals any amino acid

<400> SEQUENCE: 7

Pro Gly Ile Pro Ser Ala Cys Cys Phe Arg Val Thr Asn Ile Cys Lys
1               5                   10                  15

Ile Ser Phe Gln Ala Leu Lys Ser Tyr Lys Ile Ile Thr Ser Ser Lys
            20                  25                  30

Cys Pro Gln Thr Ala Ile Val Phe Glu Ile Lys Pro Asp Lys Met Ile
        35                  40                  45

Cys Ala Asp Pro Arg Xaa Xaa Trp Val Gln Asp Ala Lys Lys Tyr Leu
    50                  55                  60

Asp Gln Ile Ser Gln Xaa Thr Lys Pro
65                  70
```